United States Patent
Carlucci et al.

(10) Patent No.: US 6,436,080 B1
(45) Date of Patent: Aug. 20, 2002

(54) ANATOMICALLY SHAPED DISPOSABLE ABSORBENT ARTICLE WITH HIGH LOBE RESILIENCY

(75) Inventors: Giovanni Carlucci, Chieti; Olivier Corticchiato, Pescara; Roberto d'Addario, Pescara; Carlo Toro, Pescara; Carmine Cimini, Pescara, all of (IT)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 09/485,249

(22) PCT Filed: Aug. 4, 1998

(86) PCT No.: PCT/US98/17775
§ 371 (c)(1),
(2), (4) Date: Feb. 2, 2000

(87) PCT Pub. No.: WO99/07318
PCT Pub. Date: Feb. 18, 1999

(30) Foreign Application Priority Data
Aug. 5, 1997 (EP) .............................................. 97113462

(51) Int. Cl.[7] .................................................. A61F 13/15
(52) U.S. Cl. ......................... 604/385.01; 604/585.23; 428/154; 428/198; 442/394; 442/398
(58) Field of Search ........................ 604/385.23, 385.1, 604/385.01; 428/154, 198; 442/394, 398

(56) References Cited

U.S. PATENT DOCUMENTS

| 3,953,638 | A | * | 4/1976 | Kemp ........................ 428/154 |
| 4,195,634 | A | | 4/1980 | DiSalvo et al. |
| 5,129,893 | A | | 7/1992 | Thoren |
| 5,522,810 | A | | 6/1996 | Allen, Jr. et al. |
| H1698 | H | | 11/1997 | Lloyd et al. |
| 5,722,967 | A | | 3/1998 | Coles |
| 6,309,736 | B1 | * | 10/2001 | McCormack ............... 428/198 |

FOREIGN PATENT DOCUMENTS

| EP | 0 543 116 A1 | 5/1993 |
| WO | WO 91/18573 | 12/1991 |
| WO | WO 93/09744 | 5/1993 |
| WO | WO 94/09737 | 5/1994 |
| WO | WO 97/01997 | 1/1997 |

* cited by examiner

Primary Examiner—Rodney M. Lindsey
Assistant Examiner—Angela J Grayson
(74) Attorney, Agent, or Firm—Ingrid N. Hickman (57) ABSTRACT

An anatomically shaped disposable absorbent article having a front end portion and a rear end portion and a periphery, and comprising a liquid pervious topsheet, a multiplayer backsheet joined to said topsheet and an absorbent core intermediate the backsheet and the topsheet. The anatomically shaped disposable absorbent article has lobes provided by the topsheet and the backsheet extending beyond the absorbent core and has a reduced tendency to form folds in the lobes during the use.

2 Claims, 2 Drawing Sheets

ANATOMICALLY SHAPED DISPOSABLE ABSORBENT ARTICLE WITH HIGH LOBE RESILIENCY

FIELD OF THE INVENTION

The present invention relates to disposable absorbent articles. Disposable absorbent articles are considered to be absorbent devices designed to be worn externally of the body by a user and to receive fluids discharged from the body. In particular the present invention relates to disposable absorbent pantiliners, sanitary napkins, catamenials, and incontinence inserts, that are anatomically shaped and exhibit an increased ability to recover their original substantially flat configuration after folding.

BACKGROUND OF THE INVENTION

In their basic form, disposable absorbent articles comprise an absorbent core interposed between a pervious body-contacting element (alternatively referred to as a topsheet or an overwrap) and an impervious protective barrier (alternatively referred to as a backsheet). The absorbent element is, of course, intended to receive and contain the fluids discharged from the body. The body-contacting element is intended to provide comfortable and dry-feeling contact with body surfaces while allowing free passage of fluids therethrough into the absorbent element. The protective barrier is intended to prevent the fluids which are expelled or which escape from the absorbent element from soiling the user's garments.

Disposable absorbent articles are usually intended to be applied to the panty, and typically fixed to it by an adhesive, before wearing the panty with the applied absorbent article. The shape of disposable absorbent articles, as seen in plan view, has developed from a traditional, substantially rectangular shape to anatomical shapes having widths that are not constant along the length of the article and that are intended to cover additional body area as compared to a traditional rectangular product having a width corresponding to the minimum width of a shaped article. Anatomically shaped articles provide a better comfort for the user owing to their shape that better conforms to the user's anatomy, and that at the same time more closely follow the shape and contours of the panty in the crotch region, where the articles are applied, so ensuring an increased protection for the garment.

Most common anatomical shapes for disposable absorbent articles are those in which the article has a minimum width in its central portion, and is larger in its front and/or in its rear portion. The portions of the article that extend laterally in the front and/or in the rear end portion beyond this minimum width allow the absorbent article longitudinal edges to better match the contour of the panty in the crotch zone.

Such anatomically shaped disposable absorbent articles usually have an absorbent core with rectilinear, parallel longitudinal edges. The topsheet and the backsheet extend beyond the absorbent core in the portions of the absorbent article that are wider than the minimum width, and here they form lobes or ears of the article.

Disposable absorbent articles are typically applied to the user's garment in a substantially flat configuration, by "substantially flat" being meant substantially void of folds or wrinkles. During the use the article deforms and bends under the forces exerted by the user's body and by the garment, and a certain degree of deformation is indeed accepted and preferred, since it causes the absorbent article to conform to the wearer's body, therefore providing a better comfort and protection.

A disadvantage that has been experienced with anatomically shaped disposable absorbent articles comprising lobes or ears is due to the possible folding of the lobes during the use, which can cause the formation of permanent folds, generally resulting in a reduction of the useful surface of the article itself. The amount of the folding can range from few degrees, relative to the initial, substantially flat configuration, to the complete folding of a portion of a lobe, or also of the entire lobe, over or down the product. Various types of folds are possible, such as for example C-, Z-, S-, or W-shaped folds. Occurrence of such folding in the lobes of anatomically shaped absorbent articles can in fact be promoted by the longitudinal edges of the absorbent core in that they could constitute a sort of line of preferential folding for the lobes, since the article has, along these edges, a change in thickness and therefore in stiffness and resiliency. Moreover, the low overall thickness of the article can make it easier a complete folding of the lobes over or under the article itself.

This problem is less evident in traditional anatomically shaped disposable absorbent articles, where the intrinsic resiliency of the materials constituting the lobes can avoid, at least to a certain extent, the formation of permanent folds, even after a certain degree of folding has taken place, e.g. by helping the unfolding of the folded portions.

However, the problem of the formation of permanent folds in the lobes has become more evident in anatomically shaped disposable absorbent articles provided with improved backsheets comprising at least two layers laminated or otherwise joined together to make a unitary structure having specific properties.

Multilayer backsheets that are particularly preferred in disposable absorbent articles are those providing breathability.

The provision of breathable products has been considered a means for providing consumer comfort benefits in absorbent articles. Breathability has typically concentrated on the incorporation of so called "breathable backsheets" in the absorbent articles. Breathable backsheets are water vapour permeable, preferably air permeable, allowing gaseous exchange with the environment. This thereby allows for the evaporation of a portion of the fluid stored in the core and increases the circulation of air within the absorbent article. The latter is particularly beneficial as it reduces the sticky feeling experienced by many wearers during use, commonly associated with the presence of an apertured formed film or film like topsheet, particularly over extended periods of time. This is a result of topsheets designed to achieve a clean and dry appearance. These topsheets tend to be smooth thereby minimising the build up of fluid on the surface of the topsheet. However, these benefits are achieved at the expense of comfort, particularly under hot and humid conditions, when due to their smooth surface texture they tend to become sticky to the skin.

However, the main drawback associated with the use of breathable backsheets in absorbent articles is the negative effect on the protection level performance, by leakage known as wet through onto the users garment. Although, breathable backsheets in principle only allow the transfer of materials in the gaseous state, physical mechanisms such as extrusion, diffusion and capillary action may still occur and result in the transfer of the fluids from the absorbent core through the backsheet and onto the users garments. In particular, these mechanisms become more dominant if the product is utilised during physical exertion, or for heavy discharge loads or over extended periods of time. Thus, whilst the incorporation of breathable backsheets in absorbent articles is highly desirable from a comfort standpoint, since the primary role of a backsheet still remains the prevention of liquid leakage, it is necessary that such breathable backsheets are also fluid impervious in order to avoid the risk of wet through.

Dual layer breathable backsheets as those described e.g. in International Patent Applications WO 96/14037, WO 97/24095, WO 97/24096 and in European Patent Application EP 96830343.8 are particularly effective in providing both breathability and fluid imperviousness against the risk of wet through. They are particularly suitable for incorporation in thin products such as pantiliners or thin sanitary napkins. Preferred structures for such dual layer breathable backsheets usually comprise a gas permeable apertured tridimensional polymeric film, typically as the inner layer, i.e. closer to the absorbent core, adhered or in any case associated to an outer layer constituted by a gas permeable fibrous fabric layer, or, alternatively, by a gas permeable microporous polymeric layer.

Such dual layer backsheets have shown a very good behaviour in terms of breathability and wet through control, and constitute a structure that is still thin and flexible but, owing to its relative complexity, is less resilient and may increase the possibility of the formation of permanent folds in the lobes in anatomically shaped breathable products during the use. The tridimensional structure of the apertured tridimensional polymeric film for example can crush during folding and this may induce the formation of permanent or quasi permanent folds in the lobes of the shaped sanitary article during the use.

Disadvantages of the lobe folding with formation of permanent folds in the anatomically shaped disposable absorbent articles are mainly due to the decrease in the product absorbing and protecting performance caused by the reduction of the effectively useful surface area of the product, and also to the negative perception of the product quality and performance by the user when she becomes aware, usually at the time she removes the article from the garment, that the article itself has lost, to a certain extent, its initial optimal configuration. Folded lobes can moreover induce a comfort issue for the user during use of the article, since they constitute zones where the article is thicker and possibly stiffer.

It is therefore an object of the present invention to provide an anatomically shaped disposable absorbent article having a reduced tendency to form permanent folds in the lobes during the use, i.e., having a better ability to recover the initial unfolded configuration after folding.

It is a further object of the present invention to provide such an article with a reduced tendency to form permanent folds in the lobes, which is moreover breathable.

It has in fact been discovered that by controlling the joining between the superimposed layers that constitute the shaped disposable absorbent article in the lobe area it is possible to reduce the tendency of the shaped article to form permanent folds in the lobes during the use.

SUMMARY OF THE INVENTION

The present invention refers to a shaped disposable absorbent article having a front end portion and a rear end portion, and a periphery. The shaped disposable absorbent article is constituted by superimposed layers comprising a liquid pervious topsheet, a backsheet comprising at least two layers, and being joined to said topsheet at least along the periphery, and an absorbent core intermediate the topsheet and the backsheet, and has at least one lobe in at least one of the front end portion or rear end portion, the lobe being provided inside the periphery by the topsheet and the backsheet in a region where the topsheet and the backsheet extend beyond the absorbent core. The shaped disposable absorbent article has a joining ratio in the at least one lobe defined as the ratio having as the numerator the number of superimposed layers being directly joined to at least an adjacent layer in the at least one lobe other than along the periphery, and as the denominator the total number of the superimposed layers in the at least one lobe. The joining ratio has a value that is lower than or equal to 0.5.

BRIEF DESCRIPTION OF THE DRAWINGS

While the specification concludes with claims particularly pointing out and distinctly claiming the present invention, it is believed that the present invention will be better understood from the following description in conjunction with the following drawings:

DETAILED DESCRIPTION OF THE INVENTION

This invention relates to anatomically shaped disposable absorbent articles for application to the user's body, which exhibit absorbency for bodily fluids, the protection of the user's garments from soiling, and improved physical comfort to the user.

As used herein, the term "absorbent article" refers to devices which absorb and contain body exudates, and, more specifically, refers to devices which are placed against or in proximity to the body of the wearer to absorb and contain the various exudates discharged from the body. The term "disposable" is used herein to describe absorbent articles which are not intended to be laundered or otherwise restored or reused as an absorbent article (i.e., they are intended to be discarded after a single use and, preferably, to be recycled, composted or otherwise disposed of in an environmentally compatible manner). A preferred embodiment of an absorbent article of the present invention is the pantiliner 20 shown in FIG. 1. As used herein, the terms "pantiliner", and "sanitary napkin" refer to absorbent articles generally worn by females adjacent to the pudendal region that are intended to absorb and contain the various exudates which are discharged from the body (e.g., vaginal discharges, blood, menses, and urine). The present invention, however, is not limited to the particular types or configurations of absorbent articles shown in the drawings. It should be understood that the present invention is also applicable to other anatomically shaped disposable absorbent articles such as incontinent pads, and the like.

The term "use", as used herein, refers to the period of time that starts when the absorbent article is actually put in contact with the anatomy of the user.

The terms "joined", "affixed" or "secured", as used herein, encompasses configurations whereby a first member is directly connected to a second member and configurations whereby a first member is indirectly connected to a second member by connecting the first member to intermediate members which in turn are connected to the second member.

As used herein, the term "pudendal" refers to the externally visible female genitalia and is limited to the labia majora, the labia minora, the clitoris, and the vestibule.

Figure 1:
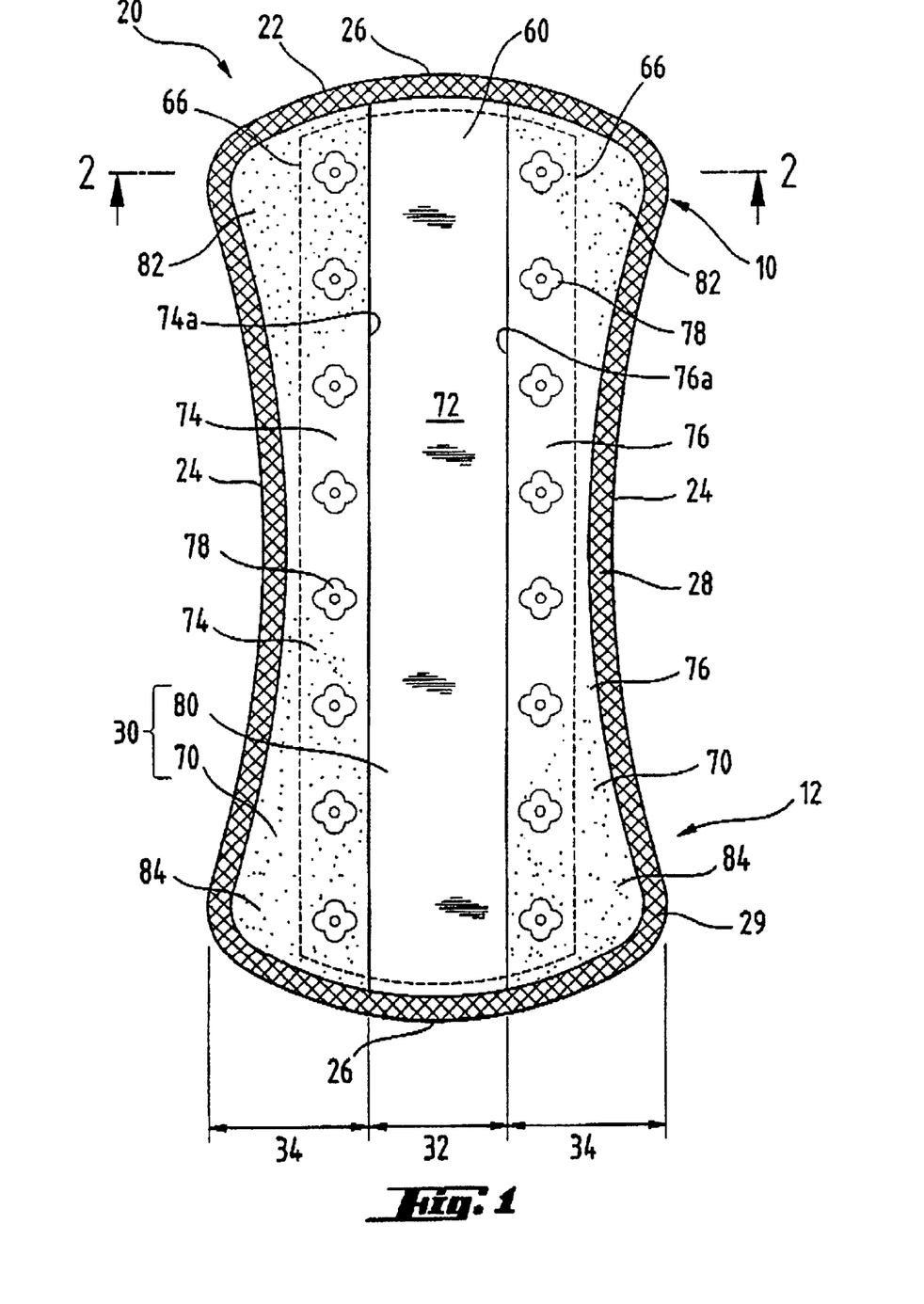
FIG. 1 is a plan view of a pantiliner according to the present invention, seen from the side thereof that faces the wearer in use.
Figure 2:
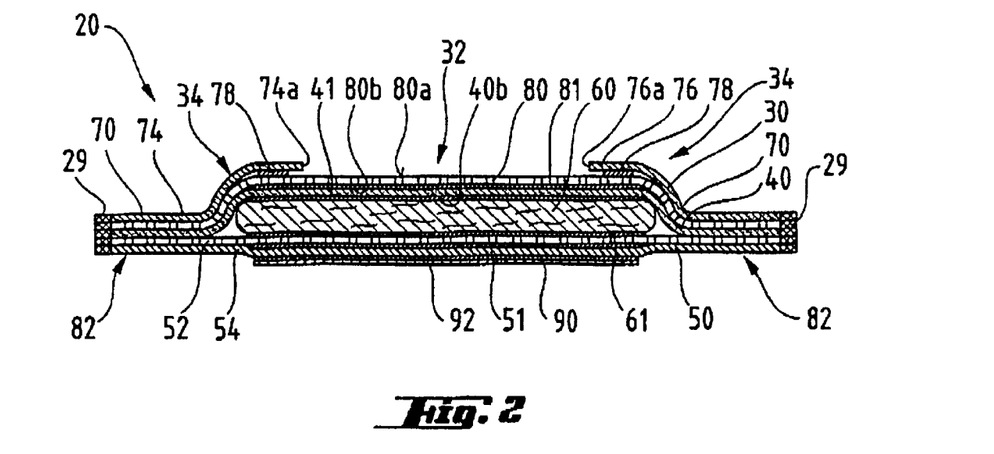
FIG. 2 is a cross-sectional view of the pantiliner of FIG. 1 on line 2—2.

As shown in FIGS. 1 and 2, the pantiliner 20 comprises an absorbent means represented by main body portion 22. The main body portion 22 has longitudinal edges 24 and lateral edges 26, together constituting the periphery 28. The term "longitudinal", as used herein, refers to a line, axis or direction in the plane of the pantiliner 20 that is generally aligned with (e.g., approximately parallel to) a vertical plane which bisects a standing wearer into left and right body halves when the pantiliner 20 is worn. The term "lateral" as used herein, refers to a line, axis or direction which lies within the plane of the pantiliner 20 that is generally perpendicular to the longitudinal direction.

The terms "front" and "rear", as used herein, refer to portions or edges in the sanitary napkin 20 that are oriented towards the front and rear part of the wearer's body, respectively, when the sanitary napkin 20 is being worn.

The main body portion 22 has a front end portion 10 and a rear end portion 12. The pantiliner 20 has concave longitudinal edges 24 to fit to the contour of the wearers panty, and therefore it is larger in both its front and rear end portions 10 and 12. In the embodiment of the present invention shown in FIG. 1 the pantiliner 20 is symmetrical both in longitudinal and in lateral direction, and therefore the front end portion 10 has substantially the same structure and shape as the rear end portion 12.

The main body portion 22 comprises a topsheet 30, a multilayer backsheet 50, and an absorbent core 60. The main body portion 22 also preferably comprises a nonwoven secondary layer 40.

The topsheet 30 is liquid permeable and when the pantiliner 20 is in use, the topsheet 30 is compliant, soft feeling, and non-irritating to the user's skin. The topsheet 30 has a central zone 32 and a pair of end zones 34. The end zones 34 extend laterally from and are contiguous with the central zone 32.

The topsheet 30 comprises a nonwoven outer layer 70 and an apertured thermoplastic film layer 80. The nonwoven outer layer 70 is liquid permeable and has an opening 72 positioned in the central zone 32. The opening 72 is provided in the nonwoven outer layer 70 as a passageway for body exudates to be deposited directly onto the apertured thermoplastic film layer 80 to take advantage of its superior fluid handling properties so that fluid will rapidly pass into the absorbent core. In a preferred embodiment, the nonwoven outer layer 70 comprises two strips 74, 76. The two strips 74, 76 of the nonwoven outer layer 70 are spaced apart on top of the apertured thermoplastic film layer 80 so that the spaced region between the two strips 74, 76 forms the opening 72. In this particular embodiment, each strip 74, 76 has approximately parallel inner edges 74a, 76a being separated apart from the lateral edge 26 to the other lateral edge 26 whereby the opening 72 has a substantially rectangular shape elongated in the longitudinal direction.

So long as the opening 72 in the center (longitudinally) of the central zone 32 is sufficiently large to permit the flow of body fluids intended to be absorbed by the core, these longitudinal ends of the central zone 32 can be covered with the nonwoven outer layer 70 or a separate layer (not shown).

The nonwoven outer layer 70 extends laterally into the seam 29 around the periphery 28 of the main body portion 22. In the embodiment illustrated in FIGS. 1 and 2 the seam 29 joins together the nonwoven outer layer 70, the apertured thermoplastic film layer 80, the nonwoven secondary layer 40 and the multilayer backsheet 50 by a known securement means, e.g. by crimping, glueing, thermobonding, or any combination thereof. The preferred pantiliner 20 has concave longitudinal edges 24 to fit to the contour of the wearers panty. In a preferred embodiment, the nonwoven outer layer 70 has a width of at least about 1.5 mm in both end zones at the narrowest portion and about at least 7–10 mm at the widest portion.

The width of the opening will depend upon the intended use of the article. For low-flow pantiliners the width of the opening is greater than about 5 mm, preferably about 10 mm to 30 mm, preferably greater than about 20 mm. For heavier-flow sanitary napkins, the width of the opening is more than about 10 mm, preferably about 20–60 mm, more preferably about 40 mm. The ratio of the width of the opening 72 to the total lateral width of the main body portion can vary based on the total width of the nonwoven outer layer 70, and of course it can also vary along the length of an anatomically shaped absorbent article such as the pantiliner 20 of the present invention. The ratio is preferably from about 4:1 to about 1:4, more preferably from about 2:1 to 1:2. It has been found that such shapes and area for the opening 72 is desirable from a product performance, process, and aesthetics standpoint. However, other shapes and various areas are possible in the design of the opening 72. For example, each strip 74, 76 can have a non-parallel inner edge, or can meet at or inward from either or both longitudinal edges 26 to define a circular opening. So long as the opening 72 is sufficiently large to permit passage of most of the fluids deposited onto the topsheet in the opening to pass, the particular arrangement or configuration of the opening is not critical.

The nonwoven outer layer 70 is preferably secured in at least partial contacting relation with the apertured thermoplastic film layer 80. The nonwoven outer layer 70 can be maintained in contact with the apertured thermoplastic film layer 80 by fusion bonding, adhesive attachment of the layers, or by any other securement means. The bonding of the nonwoven outer layer 70 to the apertured thermoplastic film layer 80 can prevent the nonwoven outer layer from being torn or from rolling back onto itself at edges 74a, 76a, thereby importing an uncomfortable feeling. Fusion bonding includes heat bonding, ultrasonic bonding, and the like. Heat bonding is the preferred means for securing the nonwoven outer layer 70 and the apertured thermoplastic film layer 80 in contacting relation. The two layers can be continuously, partially, or intermittently bonded together. In a preferred embodiment, the nonwoven outer layer 70 and the apertured thermoplastic film layer 80 are spot-bonded at a plurality of positions along the inner edge 74a, 76a of each strip 74, 76 with heat bonds 78. The heat bonds 78 provide an embossed seal pattern that can also convey an aesthetic effect in its pattern design such as a flower, a leaf, and so on.

The nonwoven outer layer 70 provides softness in the end zones of the topsheet in order to eliminate any problems of a sticky, sweaty feeling for the user as well as a member that can efficiently handle any liquids deposited onto the end zones. The nonwoven outer layer 70 comprises a nonwoven web having excellent flexibility, compliance and fluid acquisition. A suitable material for use as the nonwoven outer layer 70 of the topsheet comprises mixtures of polyethylene (the melting point of which is at a relatively low temperature), polypropylene, and/or polyester, known in the art as a "bi-component web". A layer adjacent to one surface of the nonwoven web comprises mainly bicomponent fibres (preferably 50/50 by weight) of polyethylene and polypropylene. A layer adjacent to the other surface comprises mainly bicomponent fibres (also preferably 50/50 by weight) of polyethylene and polyester. Nonwoven webs comprising fibres containing polyethylene are particularly suitable for use in the present invention because they can be readily fusion bonded. The fusion bonding between the nonwoven web and the apertured thermoplastic film layer 80 are performed by melting of the polyethylene in the fibres. Both of the above layers contain the polyethylene in the fibres so that either layer can be arranged to face toward the apertured thermoplastic film layer 80 for fusion bonding. Preferably, the layer of the nonwoven web comprising the bi-component fibres of polyethylene and polyester is arranged to face toward the apertured thermoplastic film layer 80. In this preferred arrangement, the layer of the nonwoven web comprising the bi-component fibres of polyethylene and polypropylene is arranged to face to the wearer, and provides superior flexibility compliance and soft feeling because of the character of the polypropylene. Further, the layer of the nonwoven web comprising the bi-component fibres of polyethylene and polyester perform a cushioning function. Exemplary nonwoven webs which can be used as the nonwoven outer layer 70 are available from Pantex, Italy, under the designation TB-B-23. The nonwoven outer layer can also have a plane surface or embossed pattern, as designed by the manufacture of the article. Any type of suitable non bi-component webs can also be used as the nonwoven outer layer 70.

The apertured thermoplastic film layer 80 is liquid permeable and positioned beneath the nonwoven outer layer 70 and nearer to the absorbent core 60. The apertured thermoplastic film layer 80 and the nonwoven outer layer both overlay the end zones 34. Further, the apertured thermoplastic film layer 80 is exposed through the rectangular opening 72 of the nonwoven outer layer 70 in the central zone 32 from the lateral edge 26 to the other lateral edge 26. While the apertured thermoplastic film layer 80 need not extend to the lateral or longitudinal edges of the main body portion, in a preferred embodiment as shown in FIGS. 1 and 2, the apertured thermoplastic film layer 80 extends laterally and longitudinally outward and forms a portion of the longitudinal edges 24 and lateral edges 26 or the periphery 28.

Formed films are preferred for the apertured thermoplastic film layer because they are pervious to liquids and yet non-absorbent. Thus, the surface of the formed film which is in contact with the body remains dry and is more comfortable to the wearer. Suitable formed films for the apertured thermoplastic film are described in U.S. Pat. No. 3,929,135, entitled "Absorptive Structure Having Tapered Capillaries", issued to Thompson on Dec. 30, 1975, U.S. Pat. No. 4,324,426, entitled "Disposable Absorbent Article Having A Stain-Resistant Topsheet", issued to Mullane and Smith on Apr. 13, 1982, U.S. Pat. No. 4,342,314, entitled "Resilient Plastic Web Exhibiting Fiber-Like Properties", which issued to Radel and Thompson on Aug. 3, 1982, and U.S. Pat. No. 4,463,045, entitled "Macroscopically Expanded Three-Dimensional Plastic Web Exhibiting Non-Glossy Visible Surface and Cloth-Like Tactile Impression", issued to Ahr, Louis, Mullane, and Ouellette on Jul. 31, 1984. A formed film which has been found to be satisfactory is manufactured by Tredegar Industries, Inc. of Terre Haute, Ind. under the designation X3265, and marketed as "Dri-Weave" on sanitary napkins produced by The Procter & Gamble Company of Cincinnati, Ohio.

In addition, in a preferred embodiment of the present invention, at least a portion of the outer surface (body-facing surface) 80*a* of the apertured thermoplastic film layer 80 is treated with a surfactant. It is preferred that the surfactant be substantially evenly and completely distributed at least in the central zone 32 of the outer surface 80*a* of the apertured thermoplastic film layer 80. This can be accomplished by any of the common techniques well known to those skilled in the art. For example, the surfactant can be applied to the apertured thermoplastic film layer 80 by spraying, by padding, or by the use of transfer rolls. Treating the outer surface 80*a* of the apertured thermoplastic film layer 80 with a surfactant renders the surface of the apertured thermoplastic film layer 80 more hydrophilic. This results in liquid penetrating the apertured thermoplastic film layer 80 faster than it would if the surface were not so treated. This diminishes the likelihood that body fluids will flow off the apertured thermoplastic film layer 80 rather than being absorbed by the absorbent core 60.

In a particularly preferred embodiment, an additional nonwoven secondary layer 40 is positioned between the absorbent core 60 and the apertured thermoplastic film layer 80. The nonwoven secondary layer 40 prevents "bunching'", that is, twisting of pantiliner per se, or of the absorbent core in the crotch portion which twisting can cause leakage of body exudates, and provides additional softness at the periphery 28 of the main body portion. The inner surface 80*b* of the apertured thermoplastic film layer 80 is preferably secured in contacting relation with the nonwoven secondary layer 40 by means of e.g. an adhesive layer 81. This contacting relationship results in liquid penetrating the apertured thermoplastic film layer 80 faster than if the apertured thermoplastic layer 80 were not in contact with the nonwoven secondary layer 40. The apertured thermoplastic film layer 80 can be maintained in contact with the nonwoven secondary layer 40 by, for example, heat sealing as described herein above, or by applying adhesive to the inner surface 80*b* of the apertured thermoplastic film layer 80. Preferably, the contacting relationship is applied by the same type of securement means as that between the nonwoven outer layer 70 and the apertured thermoplastic layer 80, more preferably, the same spot-bonding and heat sealing.

The nonwoven secondary layer 40 is liquid permeable and positioned between the apertured thermoplastic film layer 80 and the absorbent core 60. In one particular embodiment, the nonwoven secondary layer 40 is extended laterally and longitudinally outward and forms a portion of the longitudinal edges 24 and lateral edges 26 of the periphery 28. The material of the nonwoven secondary layer 40 can be the same as the nonwoven outer layer 70. Preferably, the surface of the nonwoven web comprising the mixture of polyethylene and polyester fibres is arranged to face towards the apertured thermoplastic film layer 80 for securement by fusion bonding in a contact relationship. In this particular embodiment, the surface 40b of the nonwoven secondary layer 40 facing the absorbent core 60 is secured in contacting relation with the absorbent core 60. The contacting relationship can be achieved by the same securement means described above for maintaining the contacting relationship between the apertured thermoplastic film layer 80 and the nonwoven secondary layer 40. Preferably, the contacting relationship is achieved by applying an adhesive 41 to face between the nonwoven secondary layer 40 and the absorbent core 60. Suitable adhesives useful for this purpose are described in U.S. Pat. No. 4,917,697. The adhesives can be applied by the same methods as described above for the surfactant applied to the outer surface 80*a* of the apertured thermoplastic film layer 80. The absorbent core 60 can be secured to the nonwoven secondary layer 40 by a uniform layer of adhesive, a patterned layer of adhesive, or an array of separate lines, spirals, or spots of adhesive. An exemplary adhesive is manufactured by Findley Adhesives Company of Wauwatosa, Wis. and designated as H-2128. The securement means between the apertured thermoplastic film layer 80 and the nonwoven secondary layer 40 will preferably comprise an open pattern network of filaments of adhesive as is disclosed in U.S. Pat. No. 4,573,986 entitled "Disposable Waste Containment Garment", issued to Minetola and Tucker on Mar. 4, 1986. An exemplary securement means of an open pattern network of filaments comprises several lines of adhesive filaments swirled into a spiral pattern such as is illustrated by the apparatus and methods shown in U.S. Pat. No. 3,911,173 issued to Sprague, Jr. on Oct. 7, 1975; U.S. Pat. No. 4,785,996 issued to Ziecker, et al. on Nov. 22, 1978; and U.S. Pat. No. 4,842,666 issued to Werenicz on Jun. 27, 1989.

The absorbent core 60 is positioned between the topsheet 30 and the multilayer backsheet 50. In a preferred embodiment of the present invention shown in FIGS. 1 and 2, the absorbent core 60 has rectilinear longitudinal edges 66 parallel to one another, and has a width that is slightly narrower than the minimum width of the pantiliner 20, so that the seam 29 along the periphery 28 of the pantiliner 20, where the topsheet 30, the multilayer backsheet 50, and the nonwoven secondary layer 40 are joined together, does not comprise anywhere the absorbent core 60. The pantiliner 20 has two lobes 82 in the front end portion 10 and two lobes 84 in the rear end portion 12, which correspond to the regions of the pantiliner 20, comprised inside the periphery 28, where at least the topsheet 30 and the multilayer backsheet 50 and, in the embodiment illustrated in FIGS. 1 and 2, also the nonwoven secondary layer 40, extend beyond the longitudinal edges 66 of the absorbent core 60.

The absorbent core 60 provides the means for absorbing body fluids. The absorbent core 60 need not have an absorbent capacity much greater than the total amount of body fluid anticipated to be absorbed. The total absorbent capacity of the absorbent core should usually be compatible with the design leading and the intended use of the absorbent article. Further, the size and absorbent capacity of the absorbent core may be varied to accommodate different uses. A pantiliner as that illustrated in FIGS. 1 and 2, for example, will have generally smaller dimensions, and will comprise an absorbent core 60 with a lower absorbent capacity, as compared to a sanitary napkin. The absorbent core 60 is generally compressible, conformable, and non-irritating to the user's skin. It can comprise any material used in the art for such purpose. Examples include comminuted wood pulp which is generally referred to as airfelt, creped cellulose wadding, absorbent foams, absorbent sponges, synthetic staple fibres, polymeric fibres, hydrogel-forming polymer absorbent gelling materials, peat moss, or any equivalent material or combinations of materials. An exemplary absorbent core is a tissue layer such as is manufactured by Ft. Howard and designated as grade 882. The absorbent core may also have a layer of absorbent gelling material, such as in the form of particles, disposed between two air-laid tissue layers (or "upper" and "lower" tissue layers). The first and second tissue layers provide containment of the absorbent gelling material, improved lateral wicking of the absorbed exudates throughout the absorbent core, and a degree of absorbency. Exemplary absorbent structures for use as the absorbent core of the present invention are described in U.S. Pat. No. 4,950,264 entitled "Thin, Flexible Sanitary Napkin" issued to Osborn on Aug. 21, 1990; U.S. Pat. No. 4,610,678 entitled "High-Density Absorbent Structures" issued to Weisman et al. on Sept. 9, 1986; U.S. Pat. No. 4,834,735 entitled "High Density Absorbent Members Having Lower Density and Lower Basis Weight Acquisition Zones", issued to Alemany et al. on May 30, 1989; and European Patent Application No. 0198 683, the Procter & Gamble Company, published Oct. 22, 1986 in the name of Duenk, et al.

Absorbent gelling materials mentioned above are those materials which, upon contact with fluids (i.e., liquids) such as water or body fluids, imbibe such fluids and thereby form hydrogels. In this manner, fluids discharged into the absorbent core 60 can be acquired and held by the absorbent gelling materials, thereby providing the articles herein with enhanced absorbent capacity and/or improved fluid retention performance. Preferred absorbent gelling materials which are employed in the absorbent core 60 will generally comprise particles of a substantially water-insoluble, slightly cross-linked, preferably neutralized, hydrogel-forming polymer material. The term "particles", as used herein, can refer to particles in any form, such as in the form of pellets, flakes, or fibres. The characteristics of the absorbent core 60 (including, but not limited to preferred types of polymer materials used herein, and types of methods which can be used for preparing these polymer particles) are described in greater detail in U.S. Pat. No. 5,009,653 issued to Osborn.

The absorbent article of the present invention may further comprise, e.g. in the absorbent core 60, an odour-control material for controlling unpleasant odours associated with absorbed body fluids.

Any known odour-control agent or any combination thereof that can be suitably included in a disposable absorbent article, including other materials such as binders and/or substrates, can be comprised in the absorbent article of the present invention as the odour-control material.

The odour-control material can be incorporated into the absorbent article by methods known in the art, for example layered on or into the absorbent core or mixed within the absorbent core. An exemplary laminated absorbent core structure comprising a layer of absorbent gelling material and of dour control material is that manufactured by Korma, Italy, under the designation KO 040.02.003.

The absorbent articles according to the present invention comprise a multilayer backsheet 50 that is impervious to liquids (e.g. vaginal discharges, menses, and/or urine) and is constituted by at least two distinct layers laminated or otherwise joined together in order to provide a backsheet structure having specific preferred properties. A multilayer backsheet comprising for example a nonwoven layer laminated to a polymeric film layer, with the nonwoven typically located on the garment facing side of the backsheet, would provide a disposable absorbent article with a more friendly and softer outer surface.

Multilayer backsheets that are particularly preferred in disposable absorbent articles according to the present invention, such as the pantiliner 20 illustrated in FIGS. 1 and 2, are those providing breathability. Preferred multilayer breathable backsheets, more particularly dual layer breathable backsheets, are those described in International Patent Applications WO 97/24095, WO 97/24096 and in European Patent Application EP 96830343.8.

In a preferred embodiment of the present invention the pantiliner 20 comprises a uni directional fluid transfer multilayer breathable backsheet 50. The primary role of the backsheet is to prevent the extrudes absorbed and contained in the absorbent structure from wetting articles that contact the absorbent product such as underpants, pants, pyjamas and undergarments. In addition however, the preferred multilayer backsheet of the absorbent article of the present invention also permits the transfer of both vapour and air through it and thus allows the circulation of air into and out of the backsheet.

The term "uni directional" as utilised herein refers to materials which have at least a substantially, if not complete, one directional fluid transport in the direction of the core, according to the definition of fluid directionality given in the above mentioned International Patent Application WO 97/24095.

Figure 3:
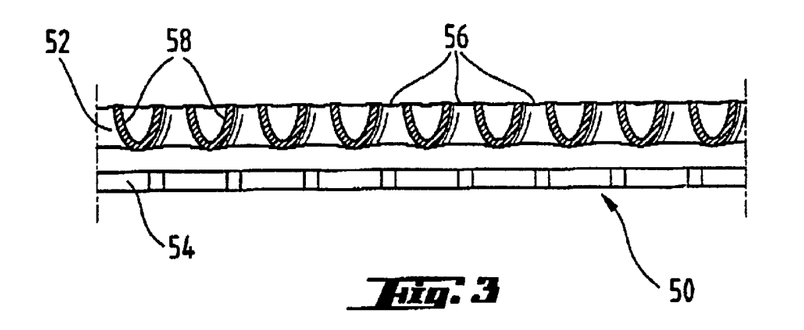
FIG. 3 is an enlarged cross-sectional view of a backsheet comprised in the pantiliner of the present invention, taken along line 2—2 of FIG. 1

In a preferred embodiment of the present invention the multilayer breathable backsheet 50, illustrated in more detail in FIG. 3, preferably comprises at least two layers; a first layer 52 comprising a gas permeable apertured polymeric film and a second layer 54 comprising a gas permeable microporous film, or alternatively, a gas permeable fibrous fabric layer. Suitable gas permeable layers can generally include 2 dimensional, planar micro and macro-porous films, macroscopically expanded films, formed apertured films and monolithic films as those described in the above mentioned three European Patent Applications. Said first and second layers 52, 54 preferably have a similar relative void volume. The first layer 52 is typically located adjacent to said core 60 and subsequent layers of the backsheet 50 are typically located further away from said core 60. The backsheet 50 may comprise additional layers. In all cases the outermost layer furthest away from the core is the outer layer. All of the layers of the backsheet 50 can be substantially in intimate and direct contact with one another.

The apertured first layer 52 of the backsheet 50 comprises a layer having discrete apertures 56 which extend beyond the horizontal plane of the garment facing surface of the layer towards the core thereby forming protuberances 58. Each protuberance has an orifice located at its terminating end. Preferably said protuberances have a funnel or conical shape, similar to those described in U.S. Pat. No. 3,929,135. The apertures located within the plane of the layer and the orifices located at the terminating end of protuberance themselves maybe circular or non circular. In any case the cross sectional dimension or area of the orifice at the termination of the protuberance is smaller than the cross sectional dimension or area of the aperture located within the plane of the layer. Preferably said apertured formed films are uni directional such that they have at least substantially, if not complete one directional fluid transport towards the core. The first layer 52 of the backsheet 50 typically has an open area of more than 5%, preferably from 10% to 35% of the total film layer area, according to the definition given in the above mentioned International Patent Application WO 97/24095.

The first layer 52 of the backsheet 50 may be made of any material known in the art, but is preferably manufactured from commonly available polymeric materials. A suitable apertured formed film include for example the material manufactured by Tredegar Industries, Inc. of Terre Haute, Ind. under the designation S225MD25.

The second layer 54 of said multilayer backsheet 50 comprises a gas permeable 2-dimensional, substantially planar apertured layer. As used herein the term 2-dimensional substantially planar refers to layers having a depth of less than 1 mm, preferably less than 0.5 mm, wherein the apertures are all within the plane of the layer. Thus, as used herein the term 2-dimensional layer does not include apertured preformed films having apertures which protrude out of the plane of the layer.

According to the present invention the apertures in said 2 dimensional layer may be of any configuration, but are preferably circular or oblong. The apertures may also be of varying dimensions. Typically, the apertures have average diameters of from 150 micrometers to 5 micrometers, preferably from 120 micrometers to 5 micrometers, most preferably from 90 micrometers to 5 micrometers. Preferably the entire surface of the 2 dimensional layer has apertures which are evenly distributed throughout the entire surface area. However, layers having only certain regions of the surface area comprising apertures such as the central portion or the peripheral portion are also possible.

The 2 dimensional apertured layer of the second layer 54 of the backsheet 50 may be made of any material known in the art, but is preferably manufactured from commonly available polymeric materials such as polyethylene or polypropylene. Suitable microporous material include XMP-1001 of Minnesota Mining and Manufacturing Company, St. Paul, Minn., USA and XBF-100W or XBF112 available from Exxon Chemicals, Ill., USA. Suitable materials are for example Goretex (TM) or Sympatex (TM) type materials well known in the art for there application in so-called breathable clothing. The apertured materials for use as a second layer 54 in the backsheet 50 may be produced using any of the methods known in the art such as described in EP 293 482 and the references therein. In addition the dimensions of the apertures produced by this method may be increased by applying a force across the plane of the backsheet layer (i.e. stretching the layer).

The second layer 54 of the backsheet 50 incorporated in the pantiliner 20 of the present invention can alternatively comprise an air permeable fibrous fabric layer composed of polymeric fibres such as polymeric nonwovens known in the art. The fibrous fibre layer preferably has a basis weight of 10 to 100 g/m$^2$, more preferably 15 to 30 g/m$^2$. The fibres can be made of any polymeric material, in particular, fibres of polyethylene, polypropylene, polyester polyacetate or combinations thereof (inter- and intra fibre combinations) and also mixtures of synthetic fibres and non absorbent natural fibres or treated natural fibres such as cotton may be utilised. The fibres are preferably spunbonded, carded or melt blown. Preferably the second layer 54 comprises a matrix of spunbonded fibres covered on one side with meltblown fibres or alternatively a matrix of meltblown fibres covered on both sides with spun blown fibres. The second layer 54 of the backsheet 50 may in addition comprise at least 5% by weight of said layer of fibres which are liquid absorptive such that the fibres swell and reduce inter-fibre spacing.

The backsheet typically extends across the whole of the absorbent structure.

The topsheet, backsheet and absorbent core elements are joined together to provide the pantiliner 20 of the present invention. At least two, preferably all of the elements of the pantiliner 20 are joined.

Each of said elements comprising at least one layer has a body facing surface and a garment facing surface. Typically, adjacent garment facing surfaces form a common interface with the body facing surface of an adjacent element or layer. The elements or layers are joined together across this common interface. In this manner the topsheet 30 is joined to the absorbent core 60, as already explained, and comprising the secondary nonwoven layer 40 therebetween, and the core 60 is joined to the backsheet 50. Furthermore, each of said topsheet 30, backsheet 50 and core 60 elements may comprise more than one layer and these layers may also be similarly joined. In addition the topsheet 30 is directly or indirectly joined to the backsheet 50 at the periphery 28 of the pantiliner 20 by means of the seam 29.

The elements and layers thereof may be joined by any means known in the art for affixing two adjacent layers of material, such that the layers are directly attached to one another or directly attached to one another via the joining means. Suitable joining means include adhesive, fusion bonding, ultra sonic bonding, stitching, heat (e.g. crimping), embossing, and/or pressure bonds, or dynamic mechanical bonds. According to an embodiment of the present invention the preferred means of joining is adhesive. Suitable adhesives include non pressure sensitive and cold adhesives. The adhesive may be applied by any means known in the art such as spiral application, slot coating, spraying, spiral spraying, curtain coating, control coating and printing, provided that the adhesive does not substantially affect the breathability.

In the preferably breathable pantiliner 20 of the present invention, the inter element or inter layer joining adhesive is selected and applied so as to reduce any impact it may have on the effective breathability of the pantiliner. Since many commonly utilised adhesives are not vapour permeable it is highly preferable to minimise the amount of adhesive used to join the layers/elements of the absorbent article in order to minimise their impact on the permeability (breathability). One means of achieving this is to use particular adhesive application methods such as open adhesive application techniques, e.g. spiral spraying, whereby areas of the common interface are adhesive free, whilst retaining the required level of attachment/joining of the two adjacent layers or elements. The layers and elements should therefore be joined in such a manner so that the absorbent article product maintains structural integrity but no more. This method finds particular application for the interlayer joining of the backsheet element layers and the joining of the backsheet element and the absorbent core element. In the embodiment of the present invention illustrated in FIG. 1 an adhesive layer 61 joins the absorbent core 60 to the first layer 52 of the dual layer backsheet 50, and an adhesive layer 61 joins together the first layer 52 and the second layer 54 of the dual layer backsheet 50. In general, adhesive layers constituted by an array of longitudinal separate lines or beads of adhesive are particularly preferred in the disposable absorbent article of the present invention since they achieve a low integration between the elements forming the article, which minimizes the impact on breathability and at the same time also provides for a lower stiffness and a better resiliency of the whole article in transverse direction. Alternatively adhesives which are vapour permeable may be used.

Preferably not more than 40%, more preferably less than 20%, most preferably less than 10% of the common interface of two adjacent layers or elements is joined. Furthermore, the density of the adhesive should be reduced and a thin application of adhesive is preferred.

In a preferred embodiment of the present invention wherein the absorbent article finds utility as a panty liner, the absorbent article is also provided with a panty fastening means which provides means to attach the article to an undergarment. For example the panty fastening means may comprise a mechanical fastener such as hook and loop fasteners such as marketed under the tradename VELCRO, snaps or holders. Alternatively, the article is fastened to the undergarment by means of panty fastening adhesive 90 on the backsheet 50. The panty fastening adhesive 90 provides a means for securing the article to the panty and preferably a means for securing the article when soiled, to the fold and wrap package for convenient disposal. Typically, at least a portion of the garment facing surface of the backsheet 50 is coated with adhesive to form the panty fastening adhesive 90. Any adhesive or glue used in the art for such purposes can be used for the panty fastening adhesive herein. Pressure sensitive adhesives are most preferred. Suitable adhesives include Century A-305-IV manufactured by the Century Adhesives Corporation of Columbus, Ohio, and Instant LOK 34-2823 manufactured by the National Starch and Chemical Company of Bridgewater, N.J., 3 Sigma 3153 manufactured by 3 Sigma and Fuller H-2238ZP manufactured by the H. B. Fuller Co.

The panty fastening adhesive 90 is typically applied to the backsheet 50 by slot coating. In order to reduce the effect on the breathability of the preferred backsheet 50 and thus of the article as a whole, the adhesive is preferably applied such that at least 60%, preferably from at least 80%, most preferably at least 90% of the surface of the backsheet 50 is adhesive free. The required adhesiveness can still be achieved even when using reduced surface coverage by using a particular distribution such as thinner strips, discontinuous strips of adhesive, intermittent dots, random patterns spirals.

The panty fastening adhesive 90 is typically covered with a removable release paper or film 92 in order to prevent the adhesive from drying out or adhering to another surface other than the panty prior to use. Any commercially available release paper or film may be used. Suitable examples include BL 30MG-A SILOX EI/O and BL 30 MG-A SILOX 4 P/O available from Akrosil Corporation.

According to the present invention, it has been discovered that by controlling in the area of the lobes 82, 84 the joining of the superimposed layers, comprising a multilayer backsheet 50, that constitute the anatomically shaped absorbent article 20 it is possible to reduce the occurrence of the formation of permanent folds in the lobes during the use the absorbent article.

The structure of the multilayer backsheet 50, particularly the structure of the preferred dual layer breathable backsheet 50 incorporated in the preferred pantiliner 20 shown in FIGS. 1 and 2, is in fact rather complex, comprising in a preferred embodiment a first layer 52 constituted by a tridimensional apertured formed film joined by known means, as explained above, to a second layer 54 constituted by a 2-dimensional apertured microporous film. Such composite structures are thin and flexible, but can, in the area of the lobes 82, 84, give rise to permanent folds when folding in the lobes occurs during the use of the pantiliner, owing to the forces exerted on the pantiliner by the user's body and by the undergarment. The tridimensional structure of the first layer 52 comprising the protuberances 58 can in fact crush during folding and this can promote the formation of permanent folds in the area of the lobes 82, 84.

According to the present invention, the joining of the superimposed layers that constitute the absorbent article has to be controlled in the area of the lobes 82, 84 of the absorbent article of the present invention. Without being bound to any theory, it is in fact believed that the presence of joining means, e.g. adhesive, between the layers in the area of the lobes, does not allow layers characterized by a better resiliency to contrast the tendency of less resilient layers to form permanent folds. On the contrary, the joining means promotes the formation of permanent or semi permanent folds in multilayer structures when folding in use occurs, by reducing the resiliency of said structures.

According to the present invention a joining ratio can be defined; said joining ratio is the ratio having as the numerator the number of the superimposed layers in the lobes 82, 84 which are directly joined to at least another adjacent layer, and as the denominator the total number of the superimposed layers in the lobes 82, 84. The values of the joining ratio can range from 0, when no joining at all is comprised between the superimposed layers in the lobe area 82, 84 other than along the periphery 28, to 1, when each of the superimposed layers in the lobe area is joined to at least another adjacent layer, possibly with all the layers joined together.

The outermost layer on either the garment facing surface or the body facing surface is considered not joined if it is not joined to the respective next inner layer in the lobes. Differently layers between these two outermost layers have to be not joined to both adjacent layers in order not to be counted in the numerator of the joining ratio.

It has been discovered that the occurrence of the formation of permanent folds in the lobes is reduced when the value of the joining ratio is lower than or equal to 0.5, preferably less than 0.2.

According to the present invention, it is also particularly preferred that the layers that constitute the multilayer backsheet 50 are not joined to each other in the area of the lobes 82, 84, other than along the periphery 28, where they are joined by the seam 29. Joining means between the layers of a multilayer backsheet, especially of a two layer breathable backsheet comprising a tridimensional apertured formed film, as that included in the preferred pantiliner 20 of the present invention, can in fact cooperate in this type of rather complex structure in inducing the formation of permanent or semi permanent folds during the use in the area of the lobes 82, 84. Upon folding the joining means is in fact likely to somehow stabilize the collapsed state of the crushed structure of the tridimensional apertured formed film constituting the first layer 52 of the preferred breathable dual layer backsheet 50.

In the preferred embodiment illustrated in FIGS. 1 and 2, where a dual layer backsheet 50 is incorporated in a pantiliner 20, the first layer 52 and the second layer 54 of the backsheet 50 are preferably not joined together in the area of the lobes 82, 84. As better shown in FIG. 2, the first layer 52 of the dual layer backsheet 50 is joined to the second layer 54 by means of a layer 51 of adhesive that does not extend in the area of the lobes 82. The first layer 52 and the second layer 54 are joined along the periphery 28 by the seam 29, that also joins the secondary nonwoven layer 40 and the layers 70, 80 of the topsheet 30.

In the preferred embodiment of the present invention illustrated in FIGS. 1 and 2 the value of the joining ratio is 0, since, as better shown in FIG. 2, none of the nonwoven outer layer 70, the apertured thermoplastic film layer 80, both constituting the topsheet 30, the nonwoven secondary layer 40, and the first and second layers 52, 54 of the dual layer breathable backsheet 50 is joined together to any other adjacent layer in the area of the lobes 82, 84. The joining means, e.g. the heat bonds 78 and the adhesive layers 41, 81, 51, and 61 do not in fact extend laterally into the area of the lobes 82 of the front end portion 10 of the pantiliner 20, as shown in FIG. 2; the same is true in the area of the lobes 84 of the rear end potion 12. All the superimposed layers constituting the pantiliner 20 are joined together by means of the seam 29, achieved e.g. by crimping, only along the periphery 28.

The control of the joining between the layers in the lobes has the effect of increasing the lobe resiliency in the anatomically shaped disposable absorbent articles of the present invention. The lobe resiliency, as defined herein, measures the capacity of the lobes of an absorbent article according to the present invention to recover from a folded configuration, i.e., to unfold, after they have been subjected to a complete folding, and it is evaluated according to the following method.

Lobe Resiliency Method

In case the panty fastening adhesive, that is usually present on the garment facing surface of the backsheet of most articles, extends into the lobe area, the products to be tested have to be prepared by removing the release paper, if present, and by deactivating the panty fastening adhesive by applying talc powder on it.

The anatomically shaped disposable absorbent article having at least one lobe is placed on a flat surface, with the garment facing surface contacting the surface;

The at least one lobe is completely folded over the body facing surface of the topsheet along a longitudinal folding line, such that a folded portion of maximum width can be achieved; in case the absorbent core has parallel rectilinear longitudinal edges, the folding line can correspond to one of said longitudinal edges; a weight exerting a pressure of 60 g/cm$^2$ is placed onto the folded lobe, completely covering the folded portion, and left in position for 3 minutes;

The weight is removed after 3 minutes and the folded portion is left free for 30 seconds;

The angle a comprised between the folded portion and the flat surface is evaluated as the angle comprised between the folded surface and the shortest segment joining the longitudinal folding line and the outermost edge of the folded portion, wherein an angle of 0° corresponds to a complete recovery of the original flat configuration (highest lobe resiliency), and an angle of 180° corresponds to a permanent fold, with no recovery (unfolding) from the folded configuration (lowest lobe resiliency).

Each result is averaged on fifteen test samples.

It has been discovered that the lobe resiliency is a good indicator to predict the behaviour in use of the lobes of an anatomically shaped disposable absorbent article, as far as the tendency to form permanent folds in the lobes is concerned.

Articles having a lobe resiliency of less than 20°, preferably less than 10°, in combination with the desired joining ratio lower than or equal to 0.5, are particularly preferred since they show a lesser tendency to remain folded, i.e., to form permanent folds in the lobes in use.

Alternative embodiments of anatomically shaped disposable absorbent articles with lobes are also comprised within the scope of the present invention, provided the joining ratio satisfy the requirements set forth above. For example embodiments comprising only two lobes, in either the front end portion or the rear end portion, or in which the topsheet comprises a single continuous layer, or, alternatively, different arrangements of the composite structure described above, such as those described in the International Patent Application WO93/09744; further, alternative embodiments are also possible in which there is no secondary nonwoven layer.

In an alternate embodiment of the present invention, the anatomically shaped disposable absorbent article comprising at least one lobe may have two flaps (not shown), each of which is adjacent to and extends laterally from the respective side edge of the absorbent core. The flaps are configured to drape over the edges of the wearer's panties in the crotch region so that the flaps are disposed between the edges of the wearer's panties and the wearer's thighs. The flaps help serve to prevent soiling of the wearer's body and panties by menstrual fluid, preferably by forming a double wall barrier along the edges of the panty. The flaps may be also provided with attachment means on their garment facing surface so that the flaps can be folded back under the panty and attached to the garment facing side of the panty.

The flaps may be constructed of various materials including materials used for the topsheet 30, backsheet 50, combinations thereof, and may be a laminate having tissue in the centre. Further, the flaps may be a separate element attached to the main body of the tridimensional absorbent article or can comprise extensions of the topsheet 30 and/or backsheet 50. It is recommended, however, that the flaps have a liquid impervious backsheet to prevent body fluids which reach the flaps from soiling the edges of the wearer's panties. Even though the area of the flaps can be considered as constituting portions of the article comprising at least the topsheet and the backsheet and extending beyond the absorbent core, it is generally meant that the flaps do not constitutes lobes, in the sense intended according to the present invention.

Preferred flaps that are suitable or adaptable to the tridimensional absorbent article of the present invention are disclosed in U.S. Pat. No. 4,687,478 issued to Van Tilburg on Aug. 18, 1987; U.S. Pat. No. 4,589,876 issued to Van Tilburg on May 20, 1986; and U.S. Pat No. 4,608,047 issued to Mattingly on Aug. 26, 1986.

Optionally, the anatomically shaped absorbent article may comprise components that naturally wrap the sides of a wearer's panties. Sanitary napkins having components that naturally wrap the sides of a wearer's panties suitable for use with the tridimensional absorbent article of the present invention are disclosed in U.S. patent application Ser. No. 08/096,121 entitled "Absorbent Article having Panty Covering Components that Naturally Wrap the Sides of Panties", filed Jul. 22, 1993, in the names of Lavash, et al and U.S. patent application Ser. No. 08/277,733 entitled "Absorbent Articles Having Undergarment Covering Components with Zones of Extensibility", filed Jul. 20, 1994, in the names of Weinberger, et al.

Although the anatomically shaped disposable absorbent article of the present invention has been described with reference to a pantiliner, it can be used beneficially in the context of other disposable absorbent articles such as sanitary napkins and incontinence articles. The disposable absorbent article may thus also have all those features and parts which are typical for products in the context of their intended use.

What is claimed is:

1. A shaped disposable absorbent article having a front end portion and a rear end portion, and a periphery, said shaped disposable absorbent article being constituted by superimposed layers comprising a liquid pervious topsheet, a backsheet comprising at least two layers, said backsheet being joined to said topsheet at least along said periphery, and an absorbent core intermediate said topsheet and said backsheet, said shaped disposable absorbent article having at least one lobe in at least one of said front end portion or rear end portion, said at least one lobe being provided inside said periphery by said topsheet and said backsheet in a region where said topsheet and said backsheet extend beyond said absorbent core, said shaped disposable absorbent article having a joining ratio in said at least one lobe defined as the ratio having as the numerator the number of said superimposed layers being directly joined to at least an adjacent layer in said at least one lobe other than along said periphery, and as the denominator the total number of said superimposed layers in said at least one lobe, said joining ratio has a value that is lower than or equal to 0.5, and said at least one lobe of said article has a lobe resiliency, as defined in the lobe resiliency test, of less than 20°.

2. A shaped disposable absorbent article according to claim 1, wherein at least one lobe said article has a lobe resiliency of less than 10°.

* * * * *